United States Patent
Gore et al.

(10) Patent No.: US 8,952,051 B2
(45) Date of Patent: Feb. 10, 2015

(54) OPHTHALMIC FORMULATIONS CONTAINING SUBSTITUTED GAMMA LACTAMS AND METHODS FOR USE THEREOF

(75) Inventors: Anuradha V. Gore, Irvine, CA (US); Robert S. Jordan, Trabuco Canyon, CA (US); Ajay Parashar, Irvine, CA (US); Chetan Pujara, Irvine, CA (US); Richard Graham, Irvine, CA (US); Mu-Lan Lee, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 695 days.

(21) Appl. No.: 12/939,846

(22) Filed: Nov. 4, 2010

(65) Prior Publication Data

US 2011/0105581 A1 May 5, 2011

Related U.S. Application Data

(60) Provisional application No. 61/258,308, filed on Nov. 5, 2009.

(51) Int. Cl.
*A61K 31/4025* (2006.01)
*A61K 9/00* (2006.01)
*A61K 47/10* (2006.01)
*A61K 47/26* (2006.01)

(52) U.S. Cl.
CPC ............ *A61K 9/0048* (2013.01); *A61K 31/4025* (2013.01); *A61K 47/10* (2013.01); *A61K 47/26* (2013.01)
USPC .......................................................... 514/422

(58) Field of Classification Search
USPC ........................................................... 514/422
See application file for complete search history.

(56) References Cited

U.S. PATENT DOCUMENTS

| 6,770,675 | B2 | 8/2004 | Reed | |
|---|---|---|---|---|
| 7,473,702 | B2 * | 1/2009 | Old et al. | ...................... 514/422 |
| 7,476,747 | B2 | 1/2009 | Old | |
| 8,293,789 | B2 * | 10/2012 | Jimenez-Bayardo et al. | 514/530 |
| 2002/0002185 | A1 | 1/2002 | Reed | |

FOREIGN PATENT DOCUMENTS

| WO | WO 98/41208 | 9/1998 |
|---|---|---|
| WO | WO 2010/041722 | 4/2010 |

OTHER PUBLICATIONS

Jiao et al: "Polyoxyethylated non10n1c surfactants and their appl1cat10ns in top1cal ocular drug de11very", Advanced Drug Delivery Reviews, Elsevier BV, Amsterdam, NL, vol. 60, No. 15, Dec. 14, 2008, pp. 1663-1673.

\* cited by examiner

*Primary Examiner* — Zohreh Fay
(74) *Attorney, Agent, or Firm* — Jonathan Y. Bass

(57) ABSTRACT

The invention provides ophthalmic formulations containing well-defined substituted gamma lactams. The formulations described herein are useful in treating a variety of ocular diseases related to ocular hypertension, such as for example, glaucoma.

34 Claims, No Drawings

OPHTHALMIC FORMULATIONS CONTAINING SUBSTITUTED GAMMA LACTAMS AND METHODS FOR USE THEREOF

PROVISIONAL PRIORITY CLAIM TO UTILITY APPLICATION

Related Application

This application claims the benefit of U.S. Provisional Application Ser. No. 61/258,308, filed Nov. 5, 2010, the disclosure of which is hereby incorporated in its entirety herein by reference.

FIELD OF THE INVENTION

The invention relates generally to ophthalmic formulations useful for treating a variety of ocular diseases and particularly to ophthalmic formulations containing well-defined substituted gamma lactams for treating ocular diseases.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain well-defined substituted γ-lactams have recently been developed for treatment of ocular hypertensive conditions (see for example U.S. Pat. No. 7,476,747). In certain cases, the substituted γ-lactams are poorly water soluble. As a result, there is a need for new formulations that will allow for topical delivery of the drug substance to the eye.

SUMMARY OF THE INVENTION

The invention provides ophthalmic formulations containing well-defined substituted gamma lactams. The formulations described herein are useful in treating a variety of ocular diseases related to ocular hypertension, such as for example, glaucoma.

In one embodiment of the invention there are provided ophthalmic formulations including at least one therapeutically active agent at a concentration of from 0.01 to 0.12% w/v (weight by volume) in an ophthalmically acceptable liquid vehicle, wherein the active agent has the structure

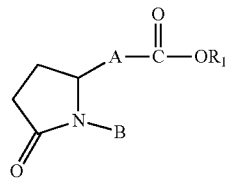

or a pharmaceutically acceptable salt thereof,
wherein
A is —(CH$_2$)$_6$—, cis-CH$_2$CH=CH—(CH$_2$)$_3$—, or —CH$_2$C≡C—(CH$_2$)$_3$—, wherein one or two CH$_2$ moieties may be substituted with S or O; or
A is —(CH$_2$)$_m$—Ar—(CH$_2$)$_o$— wherein Ar is interarylene or heterointerarylene, the sum of m and o is from 1 to 4, and wherein one or two CH$_2$ moieties may be substituted with S or O;
R$_1$ is H or C$_1$ to C$_6$ alkyl; and
B is optionally substituted aryl or optionally substituted heteroaryl.

In another embodiment there are provided articles of manufacture including a container adapted to dispense the contents of the container in metered form, wherein the contents of the container include an invention ophthalmic formulation.

In another embodiment there are provided methods for treating ocular hypertension. Such methods can be performed, for example, by administering to a subject in need thereof a formulation of the invention.

Embodiments of the present invention are described in the following paragraphs. The word "about" includes variations of concentrations of excipients and active agents which are considered to be bioequivalent by the FDA, EMEA or other regulatory agencies:

1) An ophthalmic formulation comprising at least one therapeutically active agent at a concentration of from about 0.01 to 0.12% (w/v) in an ophthalmically acceptable liquid vehicle, wherein the active agent has the structure

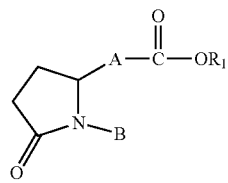

or a pharmaceutically acceptable salt thereof, wherein
A is —(CH₂)₆—, cis-CH₂CH=CH—(CH₂)₃—, or —CH₂C≡C—(CH₂)₃—, wherein one or two CH₂ moieties may be substituted with S or O; or
A is —(CH₂)ₘ—Ar—(CH₂)ₒ— wherein Ar is interarylene or heterointerarylene, the sum of m and o is from 1 to 4, and wherein one or two CH₂ moieties may be substituted with S or O;
R₁ is H or C₁ to C₆ alkyl; and
B is optionally substituted aryl or optionally substituted heteroaryl.

2. The formulation of paragraph 1 further comprising an effective amount of at least one buffer.

3. The formulation of paragraphs 1 and 2 wherein the buffer comprises phosphate, citrate, or borate.

4. The formulation of paragraphs 1, 2 and 3 wherein the buffer comprises phosphate and citrate.

5. The formulation of paragraph 2 wherein the buffer maintains the pH of the formulation between about 6.5 and about 7.5.

6. The formulation of paragraph 2 wherein the buffer maintains the pH of the formulation between about 7.0 and about 7.4.

7. The formulation of paragraph 1 further comprising at least one preservative.

8. The formulation of paragraphs 1-7 wherein the preservative is selected from the group consisting of benzalkonium chloride, chlorine dioxide, chlorobutanol, thimerosal, phenylmercuric acetate, and phenylmercuric nitrate.

9. The formulation of paragraph 8 wherein the preservative is benzalkonium chloride.

10. The formulation of paragraph 9 comprising from about 0.01 to about 0.05% (w/v) benzalkonium chloride.

11. The formulation of paragraphs 9-10 comprising from about 0.015 to about 0.025% (w/v) benzalkonium chloride.

12. The formulation of paragraphs 9-11 comprising about 0.02% (w/v) benzalkonium chloride.

13. The formulation of paragraphs 1-12 further comprising at least one tonicity agent.

14. The formulation of paragraph 13 wherein the tonicity agent is selected from the group consisting of glycerin, mannitol, sorbitol and sodium chloride.

15. The formulation of paragraphs 13-14 comprising a total concentration of tonicity agent from about 1.20 to about 1.25% (w/v).

16. The formulation of paragraphs 13-15 comprising a total concentration of tonicity agent of 1.22% (w/v).

17. The formulation of paragraphs 1-16 further comprising a solubilizer.

18. The formulation of paragraph 17 wherein the solubilizer is selected from the group polysorbate 80, hydroxy-beta-cylcodextrin, solutol, or polyoxythelene 40 stearate.

19. The formulation of paragraph 17 wherein the solubilizer is polysorbate 80.

20. The formulation of paragraphs 1-19 comprising a therapeutically active agent at a concentration of from about 0.05 to about 0.1% (w/v).

21. The formulation of paragraph 1 consisting of a therapeutically active agent at a concentration of 0.05% (w/v).

22. The formulation of paragraph 1 consisting of or consisting essentially of a therapeutically active agent at a concentration of 0.075% (w/v).

23. The formulation of paragraph 1 comprising a therapeutically active agent at a concentration of 0.01% (w/v).

24. The formulation of paragraph 1 wherein B is phenyl.

25. The formulation of paragraph 1 wherein B is alkylphenyl.

26. The formulation of paragraph 1 wherein B is hydroxyalkylphenyl.

27. The formulation of paragraph 1 wherein R₁ is C₃ alkyl.

28. The formulation of paragraph 1 wherein the therapeutically active agent has the structure:

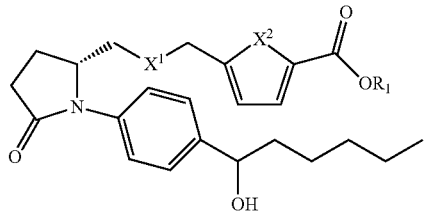

wherein X¹ and X² are independently CH₂, O, or S.

29. The formulation of paragraph 1 wherein the therapeutically active agent has the structure:

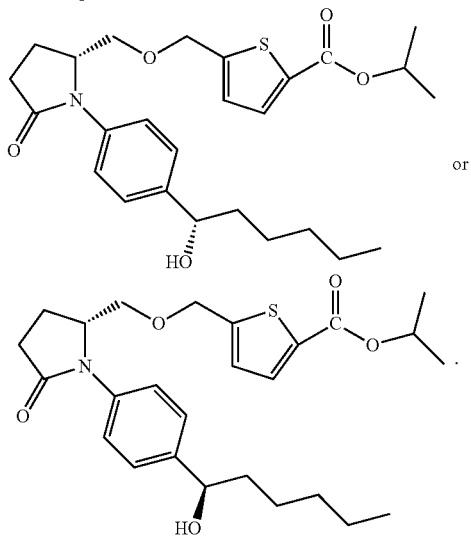

30. The formulation of paragraph 1 wherein the compound has the structure:

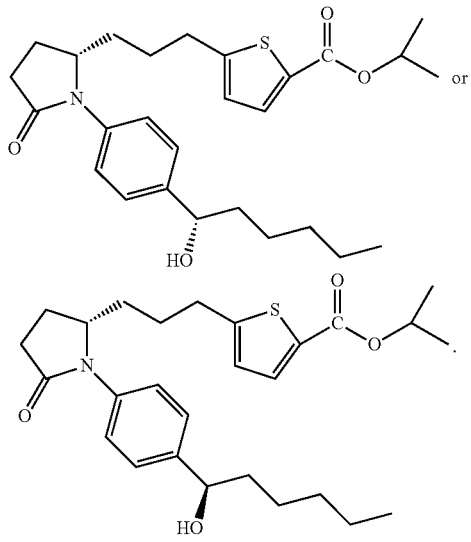

31. An article of manufacture comprising a container adapted to dispense the contents of the container in metered form, wherein the contents of the container comprise the ophthalmic formulation of paragraphs 1-30.

32. A method for treating ocular hypertension in a human patient comprising administering to a subject in need thereof a therapeutically effective amount of the formulations of paragraphs 1-30.
33. A method of lowering IOP in a patient suffering from elevated IOP comprising administering to a subject in need thereof a therapeutically effective amount of the formulations of paragraphs 1-30.
34. A method of treating glaucoma in a patient suffering from elevated IOP comprising administering to a subject in need thereof a therapeutically effective amount of the formulations of paragraphs 1-30.
35. Use of the compound of paragraphs 1-30 in the preparation of a medicament for use in treating elevated IOP or glaucoma in a human patient.
36. A formulation for lowering intraocular pressure or treating glaucoma in a patient comprising one of the following formulations selected from the table below:

| Ingredients | Units | Grade | F | G | H |
|---|---|---|---|---|---|
| Compound 1 | % w/v | | 0.05 | 0.075 | 0.1 |
| Sodium Phosphate Dibasic Heptahydrate | % w/v | USP | 0.268 | 0.268 | 0.268 |
| Citric Acid Monohydrate | % w/v | USP/Ph Eur | 0.014 | 0.014 | 0.014 |
| Polysorbate 80 (Super Refined) | % w/v | NF/Ph Eur | 1.0 | 1.0 | 1.0 |
| Mannitol | % w/v | USP/Ph Eur | 2.0 | 2.0 | 2.0 |
| Glycerin | % w/v | USP/Ph Eur | 1.2 | 1.2 | 1.2 |
| Benzalkonium Chloride | % w/v | NF/Ph Eur | 0.02 | 0.02 | 0.02 |

37. A formulation for lowering intraocular pressure or treating glaucoma in a human patient comprising one of the following formulations selected from the table below:

| Ingredients | Units | Grade | F | G | H |
|---|---|---|---|---|---|
| Compound 1 | % w/v | | About 0.05 | About 0.075 | About 0.1 |
| Sodium Phosphate Dibasic Heptahydrate or equivalent buffer | % w/v | USP | About 0.268 | About 0.268 | About 0.268 |
| Citric Acid Monohydrate or equivalent buffer | % w/v | USP/Ph Eur | About 0.014 | About 0.014 | About 0.014 |
| Polysorbate 80 (Super Refined) or equivalent solubilizer | % w/v | NF/Ph Eur | About 1.0 | About 1.0 | About 1.0 |
| Mannitol or equivalent tonicity agent | % w/v | USP/Ph Eur | About 2.0 | About 2.0 | About 2.0 |
| Glycerin or equivalent tonicity agent | % w/v | USP/Ph Eur | About 1.2 | About 1.2 | About 1.2 |
| Benzalkonium Chloride or equivalent preservative | % w/v | NF/Ph Eur | About 0.02 | About 0.02 | About 0.02 |

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —CH$_2$O$R_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

As used herein "interarylene" or "heterointerarylene" refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

It will be readily apparent to those skilled in the art that some of the therapeutically active agents of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the therapeutically active agents of the invention may form salts with pharmaceutically acceptable acids or bases, and such pharmaceutically acceptable salts of the compounds described herein are also within the scope of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

The invention provides ophthalmic formulations including at least one therapeutically active agent at a concentration of from 0.01 to 0.12% (w/v) in an ophthalmically acceptable liquid vehicle, wherein the active agent has the structure

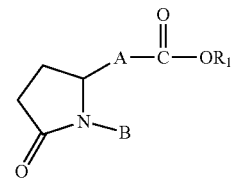

or a pharmaceutically acceptable salt thereof,
wherein
A is —$(CH_2)_6$—, cis-$CH_2CH=CH$—$(CH_2)_3$—, or —$CH_2C\equiv C$—$(CH_2)_3$—, wherein one or two $CH_2$ moieties may be substituted with S or O; or A is —$(CH_2)_m$—Ar—$(CH_2)_o$— wherein Ar is interarylene or heterointerarylene, the sum of m and o is from 1 to 4, and wherein one or two $CH_2$ moieties may be substituted with S or O;

$R_1$ is H or $C_1$ to $C_6$ alkyl; and

B is optionally substituted aryl or optionally substituted heteroaryl.

In some embodiments, B is phenyl, alkylphenyl, or hydroxyalkylphenyl. In one embodiment, B is 1-hydroxyhexyl.

In some embodiments $R_1$ is $C_1$-$C_3$ alkyl. In one embodiment, $R_1$ is isopropyl.

In some embodiments the therapeutically active agent has the structure:

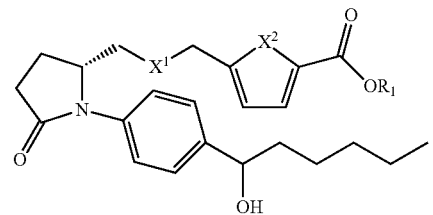

wherein $X^1$ and $X^2$ are independently $CH_2$, O, or S.

Exemplary therapeutically active agents contemplated for use in the practice of the invention include, but are not limited to,

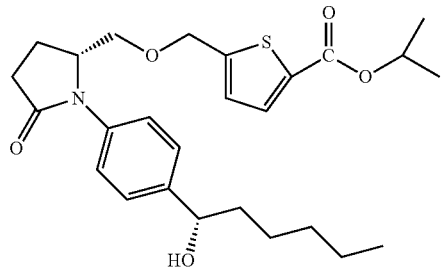

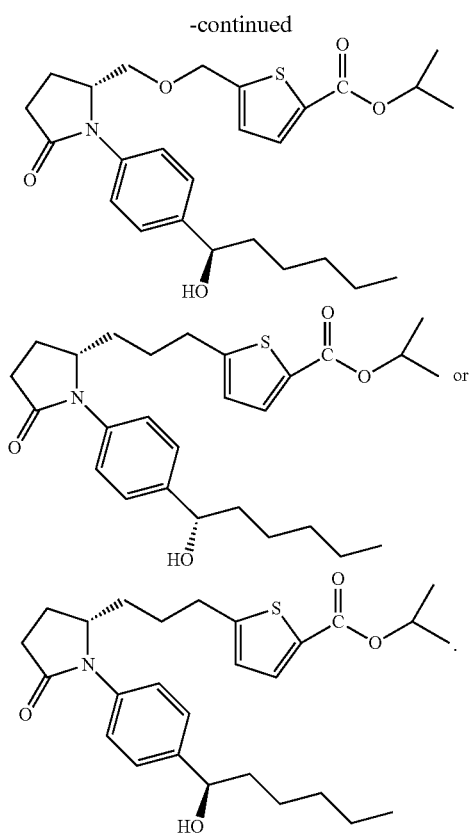

An effective amount of at least one therapeutically active agent in the ophthalmic formulation disclosed herein is an amount useful to observe a therapeutic effect as compared to a placebo formulation that, except for the absence of the therapeutically active agent, is otherwise identical to the formulation. The amount of therapeutically active agent to administer depends on factors such as the intended therapeutic effects, the specific mammal in need thereof, the severity and nature of the mammal's condition, the manner of administration, the potency and pharmacodynamics of the particular compound, and the judgment of the prescribing physician. In some embodiments of the invention, the therapeutically active agent is present at a concentration of 0.01 to 0.12% w/v. In other embodiments, the therapeutically active agent is present at a concentration of 0.05 to 0.1% (w/v). In certain embodiments, the therapeutically active agent is present at a concentration of 0.05%, 0.075%, or 0.01% (w/v).

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants. The formulations or compositions of the present invention maybe in the form of solutions, emulsions, reverse-emulsions, micro-emulsions or delivered by a bioerodable or non-bioerodable device or ocular implant.

As is known in the art, buffers are commonly used to adjust the pH to a desirable range for ophthalmic use. Generally, a pH of around 6-8 is desired, however, this may need to be adjusted due to considerations such as the stability or solubility of the therapeutically active agent or other excipients. In some embodiments of the invention, the buffer maintains the pH between 6.5 and 7.5. In other embodiments, the buffer maintains the pH between 7.0 and 7.4. Many buffers including salts of inorganic acids such as phosphate, borate, and sulfate are known. In some embodiments of the invention a phosphate/phosphoric acid buffer is used in the formulations described herein. The term "phosphate/phosphoric acid" refers to any combination of phosphoric acid and one or more of the conjugate bases such that the pH is adjusted to the desired range. In other embodiments borate/boric acid buffer is used. In still other embodiments a citrate/citric acid buffer is used in the formulations described herein. In certain embodiments a combination of phosphate/phosphoric acid buffer and citrate/citric acid buffer is used in the formulations described herein.

In ophthalmically acceptable liquids tonicity agents often are used to adjust the composition of the formulation to the desired isotonic range. Tonicity agents are well known in the art and some examples include glycerin, mannitol, sorbitol, sodium chloride, and other electrolytes. In some embodiments of the invention, the tonicity agent is present in the formulation at a concentration of 1.20 to 1.25% w/v. In one embodiment, the tonicity agent is present at a concentration of 1.22% w/v.

A surfactant may be used for assisting in dissolving an excipient or a therapeutically active agent, dispersing a solid or liquid in a composition, enhancing wetting, modifying drop size, or a number of other purposes. Useful surfactants, include, but are not limited to sorbitan esters, Polysorbate 20, Polysorbate 40, Polysorbate 60, Polysorbate 80, stearates, glyceryl stearate, isopropyl stearate, polyoxyl stearate, propylene glycol stearate, sucrose stearate, polyethylene glycol, polyethylene oxide, polypropylene oxide, polyethylene oxide-polypropylene oxide copolymers, alcohol ethoxylates, alkylphenol ethoxylates, alkyl glycosides, alkyl polyglycosides, fatty alcohols, phosphalipids, phosphatidyl chloline, phosphatidyl serine, and the like.

Other excipient components which may be included in the ophthalmic preparations are chelating agents. A useful chelating agent is edetate disodium, although other chelating agents may also be used in place or in conjunction with it.

Preservatives are used in multi-use ophthalmic compositions to prevent microbial contamination of the composition after the packaging has been opened. A number of preservatives have been developed including quaternary ammonium salts such as benzalkonium chloride; mercury compounds such as phenylmercuric acetate and thimerosal; alcohols such as chlorobutanol and benzyl alcohol; and others. In one embodiment of the invention, the preservative is benzalkonium chloride. Benzalkonium chloride is present in the invention formulations from 0.01 to 0.05% (w/v). In other embodiments the concentration is 0.015 to 0.025 (w/v). In certain embodiments, the concentration is 0.02% (w/v).

The following examples are intended only to illustrate the invention and should in no way be construed as limiting the invention.

EXAMPLES

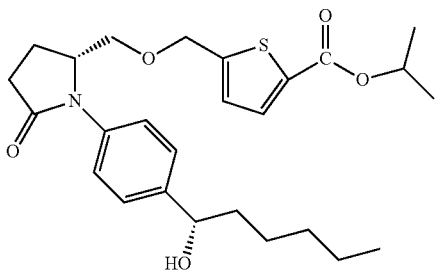

Compound 1

Compound 1 is a poorly water-soluble therapeutically active agent intended for topical delivery to the eye for treatment of glaucoma. Excipients which can enhance the solubility of this drug molecule in aqueous media need to be utilized to formulate this material at dose strengths sufficient for its intraocular pressure (IOP) reducing effect. The main solubilizer used was Polysorbate 80, which significantly enhances the solubility of Compound 1 in aqueous media. Other solubilizers that were evaluated included hydroxy-beta-cylcodextrin, solutol and polyoxythelene 40 stearate. Both preserved and preservative-free formulations were developed for use either with packaging in multi-dose dropper bottles or unit dose vials. Benzalkonium chloride (BAK) was used as an antimicrobial preservative to enable multi-dose packaging configurations.

Example 1

Preserved formulations are shown in Table 1, while preservative-free formulations are shown in Table 2.

Formulations shown in Table 1 were prepared as follows. Purified water (about 80% of batch size) was measured into an appropriately sized mixing container. Vigorous mixing was started using an overhead mixer (Rotosolver) to form a strong vortex. The following ingredients were added into the vortex in order shown, allowing each to dissolve before the next addition: sodium chloride, sodium phosphate, citric acid and benzalkonium chloride. The pH was checked and adjusted as needed with dilute hydrochloric acid or sodium hydroxide solution to pH 7.3. Compound 1 was added during vigorous mixing and mixing was continued for 30-35 minutes so that the solution was clear. Purified water was added to correct the final volume. The solution was sterilized by passage through a sterile filtration apparatus fitted with a 0.2 μm membrane.

TABLE 1

Examples of Preserved Formulations for Compound 1

| Ingredients | Units | Grade | Formulation A | Formulation B |
|---|---|---|---|---|
| Compound 1 | % w/v | | Range 0.01 to 0.1 | Range 0.01 to 0.1 |
| Sodium Phosphate Dibasic Heptahydrate | % w/v | USP | 0.268 | 0.268 |
| Citric Acid Monohydrate | % w/v | USP/Ph Eur | 0.014 | 0.014 |
| Polysorbate 80 (Super Refined) | % w/v | NF/Ph Eur | 1.0 | 1.0 |
| Mannitol | % w/v | USP/Ph Eur | 2.0 | 4.25 |
| Glycerin | % w/v | USP/Ph Eur | 1.2 | — |
| Benzalkonium Chloride | % w/v | NF/Ph Eur | 0.02 | 0.02 |
| Edetate disodium | % w/v | USP/Ph Eur | 0.01 | 0.01 |
| NaOH/HCl | pH | NF/Ph Eur | 7.4 | 7.4 |
| Purified Water/WFI | Q.S. | USP/Ph Eur | QS | QS |

TABLE 2

Examples of Preservative-free (Unit Dose) Formulations for Compound 1

| Ingredients | Units | Grade | Formulation C | Formulation D |
|---|---|---|---|---|
| Compound 1 | % w/v | | Range 0.01 to 0.1 | Range 0.01 to 0.1 |
| Sodium Phosphate Dibasic Heptahydrate | % w/v | USP | 0.268 | 0.268 |
| Citric Acid Monohydrate | % w/v | USP/Ph Eur | 0.014 | 0.014 |
| Polysorbate 80 (Super Refined) | % w/v | NF/Ph Eur | 1.0 | 1.0 |
| Mannitol | % w/v | USP/Ph Eur | 2.0 | 4.25 |
| Glycerin | % w/v | USP/Ph Eur | 1.2 | — |
| NaOH/HCl | pH | NF/Ph Eur | 7.4 | 7.4 |
| Purified Water/WFI | Q.S. | USP/Ph Eur | QS | QS |

Example 2

During the development of the preserved formulations, it was observed that in presence of polysorbate 80, the antimicrobial effect of BAK is greatly reduced. This effect was proportional to the level of solubilizer present in the formulations, and at lower levels of polysorbate 80, improved efficacy of BAK was seen (Table 3). However, lower level of polysorbate 80 is not sufficient to solubilize Compound 1 at the concentrations required for the clinical and toxicology studies.

TABLE 3

Antimicrobial Preservative Efficacy Test (APET) results showing effect of Polysorbate 80 on Antimicrobial efficacy of BAK in presence of sodium chloride

| # | Buffer species | Tonicity agent | PS80 | EDTA (% w/w) | BAK conc. ppm | PET criteria* PhEur A | PhEur B | USP |
|---|---|---|---|---|---|---|---|---|
| 1 | Cit-PO4 | NaCl | 0.2 | — | 200 | Pass | Pass | Pass |
| 2 | buffer | NaCl | 0.5 | — | 200 | Fail | Fail | Fail |
| 3 | pH 7.4 | NaCl | 0.5 | 0.1 | 200 | Fail | Fail | Pass |
| 15 | | NaCl | 1.0 | — | 200 | Fail | Fail | Fail |

*Final results after 28 days

Example 4

Replacing the sodium chloride in the formulations with mannitol or glycerin as tonicity agent greatly enhances the antimicrobial efficacy of BAK. Using these agents in the formulation, it was thus possible to meet the compendial criteria for Antimicrobial Preservative Efficacy Test (APET). Examples of APET results for some of these formulations are presented in Table 4. Addition of ethylene diamine tetraacetic acid (EDTA) further enhances the antimicrobial efficacy of BAK, especially with respect to the *Pseudomonas* organisms.

TABLE 4

Antimicrobial Preservative Efficacy Test (APET) results showing effect of Polysorbate 80 on Antimicrobial efficacy of BAK when sodium chloride is replaced by glycerin and/or mannitol

| # | Buffer species | Buffer conc (mM) | Tonicity agent | EDTA (% w/w) | BAK conc. ppm | PET criteria* PhEur A | PhEur B | USP |
|---|---|---|---|---|---|---|---|---|
| 25 | Cit-PO4 buffer | 10 | Mannitol/ | 0.01 | 120 | Fail | Fail | Pass |
| 26 | pH 7.4 with | 10 | glycerin | 0.01 | 140 | Fail | Pass | Pass |
| 27 | 1% PS80 | 10 | | 0.01 | 160 | Pass | Pass | Pass |
| 28 | | 10 | | 0.01 | 180 | Pass | Pass | Pass |
| 29 | | 10 | | 0.01 | 200 | Pass | Pass | Pass |
| 30 | | 10 | | 0.01 | 240 | Pass | Pass | Pass |
| 40 | Cit-PO4 buffer | 10 | Mannitol/ | — | 145 | Fail | Pass | Pass |
| 41 | pH 7.4 with | 10 | glycerin | — | 157 | Pass | Pass | Pass |
| 42 | 1% PS80 | 10 | | — | 165 | Pass | Pass | Pass |
| 43 | | 10 | | — | 186 | Pass | Pass | Pass |
| 44 | | 10 | | — | 201 | Pass | Pass | Pass |

*Final results after 28 days

Example 5

Exemplary invention formulations for Compound 1 are thus composed of the therapeutically active agent (Compound 1) dissolved in an aqueous vehicle containing Polysorbate 80 as solubilizer, buffer comprised of phosphate and citrate species, buffer concentration restricted to 10 mM, glycerin and/or mannitol as tonicity agents and BAK at levels above 170 ppm as the antimicrobial preservative. EDTA is included in the formulation since it enhances the antimicrobial effectiveness of BAK. Formulation compositions selected for use in Clinical and toxicology studies are listed in Table 5.

TABLE 5

Preserved Formulations

| Ingredients | Units | Grade | E | F | G | H | I |
|---|---|---|---|---|---|---|---|
| Compound 1 | % w/v | | 0.025 | 0.05 | 0.075 | 0.1 | 0.12 |
| Sodium Phosphate Dibasic Heptahydrate | % w/v | USP | 0.268 | 0.268 | 0.268 | 0.268 | 0.268 |
| Citric Acid Monohydrate | % w/v | USP/Ph Eur | 0.014 | 0.014 | 0.014 | 0.014 | 0.014 |
| Polysorbate 80 (Super Refined) | % w/v | NF/Ph Eur | 1.0 | 1.0 | 1.0 | 1.0 | 1.0 |
| Mannitol | % w/v | USP/Ph Eur | 2.0 | 2.0 | 2.0 | 2.0 | 2.0 |
| Glycerin | % w/v | USP/Ph Eur | 1.2 | 1.2 | 1.2 | 1.2 | 1.2 |
| Benzalkonium Chloride | % w/v | NF/Ph Eur | 0.02 | 0.02 | 0.02 | 0.02 | 0.02 |
| Edetate disodium | % w/v | USP/Ph Eur | 0.01 | 0.01 | 0.01 | 0.01 | 0.01 |
| NaOH/HCl | pH | NF/Ph Eur | 7.4 | 7.4 | 7.4 | 7.4 | 7.4 |
| Purified Water/WFI | Q.S. | USP/Ph Eur | QS | QS | QS | QS | QS |

Example 6

Compositions of preservative-free formulations intended as unit dose products are listed in Table 6.

TABLE 6

Preservative-free Formulations Intended for Use as Unit Dose Formulations

| Ingredients | Units | Grade | Example | J | K |
|---|---|---|---|---|---|
| Compound 1 | % w/v | | 0.01 to 0.12 | 0.025 | 0.1 |
| Sodium Phosphate Dibasic Heptahydrate | % w/v | USP | 0.268 | 0.268 | 0.268 |
| Citric Acid Monohydrate | % w/v | USP/Ph Eur | 0.014 | 0.014 | 0.014 |
| Polysorbate 80 (Super Refined) | % w/v | NF/Ph Eur | 1.0 | 1.0 | 1.0 |
| Mannitol | % w/v | USP/Ph Eur | 2.0 | 2.0 | 2.0 |
| Glycerin | % w/v | USP/Ph Eur | 1.2 | 1.2 | 1.2 |
| NaOH/HCl | pH | NF/Ph Eur | 7.4 | 7.4 | 7.4 |
| Purified Water/WFI | Q.S. | USP/Ph Eur | QS | QS | QS |

Example 7

In Vivo Data

Effect of Formulations in Dog IOP Lowering Study.

TABLE 7

Examples of formulation Compositions for Dog IOP lowering study

| Ingredients | L % (w/v) | M % (w/v) |
|---|---|---|
| Compound 1 | 0.05 | 0.05 |
| Benzalkonium Chloride (BAK) | — | 0.02 |
| Sodium Phosphate Dibasic Heptahydrate | 0.22 | 0.268 |
| Sodium Phosphate Monobasic Monohydrate | 0.026 | — |
| Citric Acid Monohydrate | — | 0.014 |
| Sodium Chloride | 0.82 | — |
| Mannitol | — | 2.0 |
| Glycerin | — | 1.2 |
| Polysorbate 80 | 1.0 | 1.0 |
| 1N NaOH/1N HCl | 7.4 | 7.4 |
| Purified Water | QS | QS |

Good IOP Lowering Effect of Formulations Observed.

TABLE 8

Effects of Compound 1 0.05%, Formulations L vs M
and Given Once Daily, on Dog Intraocular Pressure

| | | Intraocular Pressure (mm Hg) at Predetermined Times (HR) | | | | | | | | | |
|---|---|---|---|---|---|---|---|---|---|---|---|
| | | 0 | 2 | 4 | 6 | 24 | 26 | 28 | 30 | 48 | 50 |
| Compound 1 in L-treated Eye | Mean X | 13.7 | 10.9 | 10.2 | 8.4 | 10.9 | 9.5 | 9.0 | 8.4 | 10.7 | 10.2 |
| | ±SEM | 0.7 | 0.6 | 0.8 | 0.8 | 0.6 | 0.4 | 0.7 | 0.5 | 0.4 | 0.6 |
| Compound 1 in M-treated Eye | Mean X | 13.2 | 10.3 | 8.7 | 8.3 | 10.4 | 9.4 | 9.1 | 8.7 | 10.4 | 9.9 |
| | ±SEM | 0.4 | 0.7 | 0.9 | 1.0 | 0.6 | 0.6 | 0.7 | 0.6 | 0.4 | 0.7 |

| | | Difference from Baseline IOP (mm Hg) at Times (HR) | | | | | | | | | |
|---|---|---|---|---|---|---|---|---|---|---|---|
| | | 0 | 2 | 4 | 6 | 24 | 26 | 28 | 30 | 48 | 50 |
| Compound 1 in L-treated Eye | Mean X | 0 | −2.9* | −3.5* | −5.4* | −2.9* | −4.2* | −4.7* | −5.4* | −3.0* | −3.5* |
| | ±SEM | 0 | 0.8 | 1.0 | 0.9 | 0.3 | 0.5 | 0.7 | 0.7 | 0.3 | 0.7 |
| Compound 1 in M-treated Eye | Mean X | 0 | −2.9* | −4.5* | −4.9* | −2.9* | −3.9* | −4.1* | −4.5* | −2.8* | −3.3* |
| | ±SEM | 0 | 0.6 | 0.8 | 0.8 | 0.5 | 0.4 | 0.6 | 0.6 | 0.5 | 0.6 |

| | | Intraocular Pressure (mm Hg) at Predetermined Times (HR) | | | | | | | | | |
|---|---|---|---|---|---|---|---|---|---|---|---|
| | | 52 | 54 | 72 | 74 | 76 | 78 | 96 | 98 | 100 | 102 |
| Compound 1 in L-treated Eye | Mean X | 9.6 | 8.8 | 11.4 | 10.2 | 9.6 | 9.9 | 11.0 | 10.0 | 9.1 | 9.1 |
| | ±SEM | 0.4 | 0.6 | 0.6 | 0.8 | 0.6 | 0.6 | 0.7 | 0.5 | 0.6 | 0.4 |
| Compound 1 in M-treated Eye | Mean X | 9.1 | 8.5 | 10.3 | 9.2 | 8.9 | 8.9 | 10.3 | 9.4 | 8.9 | 8.7 |
| | ±SEM | 0.4 | 0.7 | 0.7 | 0.5 | 0.4 | 0.4 | 0.7 | 0.3 | 0.6 | 0.4 |

| | | Difference from Baseline IOP (mm Hg) at Times (HR) | | | | | | | | | |
|---|---|---|---|---|---|---|---|---|---|---|---|
| | | 52 | 54 | 72 | 74 | 76 | 78 | 96 | 98 | 100 | 102 |
| Compound 1 in L-treated Eye | Mean X | −4.1* | −4.9* | −2.4* | −3.5* | −4.1* | −3.9* | −2.7* | −3.7* | −4.6* | −4.6* |
| | ±SEM | 0.7 | 0.7 | 0.5 | 0.6 | 0.4 | 0.4 | 0.3 | 0.5 | 0.6 | 0.6 |
| Compound 1 in M-treated Eye | Mean X | −4.1* | −4.7* | −2.9* | −4.0* | −4.3* | −4.4* | −2.9* | −3.8* | −4.3* | −4.5* |
| | ±SEM | 0.3 | 0.5 | 0.6 | 0.4 | 0.3 | 0.4 | 0.6 | 0.4 | 0.6 | 0.2 |

*p < 0.05 according to Student's paired t-test comparing responses to baseline (time 0 readings)
n = 7 (year of study, 2009)

Example 8

A 44 year old Caucasian male suffering from glaucoma administers Formulation F of Table 5 to the eye once daily for a period of 45 days. Hours after applying the 0.05% active agent formulation each day, a 30% reduction in intraocular pressure (IOP) is observed.

Example 9

A 53 year old African-American male suffering from glaucoma administers Formulation G of Table 5 to the eye once daily for a period of 30 days. Hours after applying the 0.075% active agent formulation each day, a 36% reduction in intraocular pressure (IOP) is observed.

Example 10

A 47 year old Hispanic female suffering from glaucoma administers Formulation H of Table 5 to the eye once daily for a period of 25 days. Hours after applying the 0.1% active agent formulation each day, a 42% reduction in intraocular pressure (IOP) is observed.

While this invention has been described with respect to these specific examples, it is understood that other modifications and variations are possible without departing from the spirit of the invention.

What is claimed is:

1. An ophthalmic formulation comprising at least one therapeutically active agent at a concentration of from 0.01 to 0.12% (w/v) in an ophthalmically acceptable liquid vehicle, wherein the active agent has the structure:

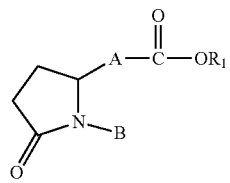

or a pharmaceutically acceptable salt thereof,
wherein:
A is $-(CH_2)_6-$, cis-$CH_2CH=CH-(CH_2)_3-$, or $-CH_2C\equiv C-(CH_2)_3-$, wherein one or two $CH_2$ moieties may be substituted with S or O; or
A is $-(CH_2)_m-Ar-(CH_2)_o-$ wherein Ar is interarylene or heterointerarylene, the sum of m and o is from 1 to 4, and wherein one or two $CH_2$ moieties are substituted with S or O;
$R_1$ is H or $C_1$ to $C_6$ alkyl; and
B is optionally substituted aryl or optionally substituted heteroaryl.

2. The formulation of claim 1 further comprising an effective amount of at least one buffer.

3. The formulation of claim 2 wherein the buffer comprises phosphate, citrate, or borate.

4. The formulation of claim 3 wherein the buffer comprises phosphate and citrate.

5. The formulation of claim 2 wherein the buffer maintains the pH of the formulation between 6.5 and 7.5.

6. The formulation of claim 2 wherein the buffer maintains the pH of the formulation between 7.0 and 7.4.

7. The formulation of claim 1 further comprising at least one preservative.

8. The formulation of claim 7 wherein the preservative is selected from the group consisting of benzalkonium chloride, chlorine dioxide, chlorobutanol, thimerosal, phenylmercuric acetate, and phenylmercuric nitrate.

9. The formulation of claim 8 wherein the preservative is benzalkonium chloride.

10. The formulation of claim 9 comprising from 0.01 to 0.05% (w/v) benzalkonium chloride.

11. The formulation of claim 9 comprising from 0.015 to 0.025% (w/v) benzalkonium chloride.

12. The formulation of claim 9 comprising 0.02% (w/v) benzalkonium chloride.

13. The formulation of claim 1 further comprising at least one tonicity agent.

14. The formulation of claim 13 wherein the tonicity agent is selected from the group consisting of glycerin, mannitol, sorbitol or sodium chloride.

15. The formulation of claim 13 comprising a total concentration of tonicity agent from 1.20 to 1.25% (w/v).

16. The formulation of claim 13 comprising a total concentration of tonicity agent of 1.22% (w/v).

17. The formulation of claim 1 further comprising a solubilizer.

18. The formulation of claim 17 wherein the solubilizer is polysorbate 80, hydroxy-beta-cylcodextrin, solutol, or polyoxythelene 40 stearate.

19. The formulation of claim 17 wherein the solubilizer is polysorbate 80.

20. The formulation of claim 1 comprising a therapeutically active agent at a concentration of from 0.05 to 0.1% (w/v).

21. The formulation of claim 1 comprising a therapeutically active agent at a concentration of 0.05% (w/v).

22. The formulation of claim 1 comprising a therapeutically active agent at a concentration of 0.075% (w/v).

23. The formulation of claim 1 comprising a therapeutically active agent at a concentration of 0.01% (w/v).

24. The formulation of claim 1 wherein B is phenyl.

25. The formulation of claim 1 wherein B is alkylphenyl.

26. The formulation of claim 1 wherein B is hydroxyalkylphenyl.

27. The formulation of claim 1 wherein $R_1$ is $C_3$ alkyl.

28. The formulation of claim 1 wherein the therapeutically active agent has the structure:

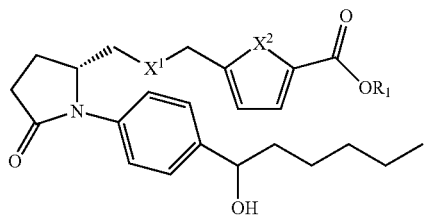

or a pharmaceutically acceptable salt thereof, wherein $X^1$ is O or S and $X^2$ is independently $CH_2$, O, or S.

29. An ophthalmic formulation of comprising at least one therapeutically active agent at a concentration of from 0.01 to 0.12% (w/v) in an ophthalmically acceptable liquid vehicle, wherein the therapeutically active agent has the structure:

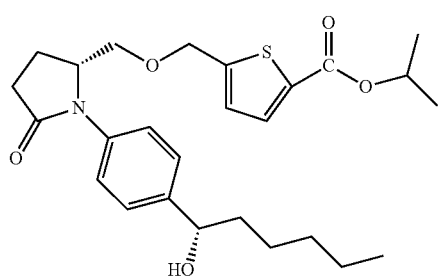 [SMILES: CCCCC[C@H](O)c1ccc(N2C(=O)CC[C@@H]2COCc2ccc(C(=O)OC(C)C)s2)cc1]

or a pharmaceutically acceptable salt thereof, or

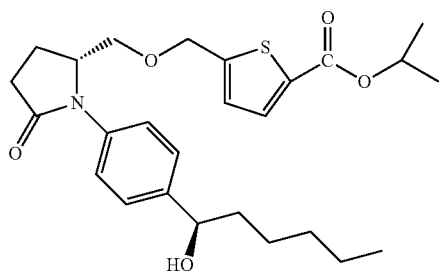 [SMILES: CCCCC[C@@H](O)c1ccc(N2C(=O)CC[C@@H]2COCc2ccc(C(=O)OC(C)C)s2)cc1]

or a pharmaceutically acceptable salt thereof.

30. An ophthalmic formulation of comprising at least one therapeutically active agent at a concentration of from 0.01 to 0.12% (w/v) in an ophthalmically acceptable liquid vehicle, wherein the therapeutically active agent has the structure:

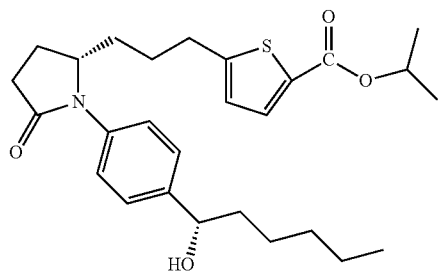 [SMILES: CCCCC[C@H](O)c1ccc(N2C(=O)CC[C@@H]2CCCc2ccc(C(=O)OC(C)C)s2)cc1]

or a pharmaceutically acceptable salt thereof, or

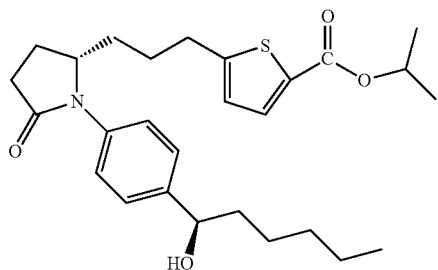 [SMILES: CCCCC[C@@H](O)c1ccc(N2C(=O)CC[C@@H]2CCCc2ccc(C(=O)OC(C)C)s2)cc1]

or a pharmaceutically acceptable salt thereof.

31. An article of manufacture comprising a container adapted to dispense the contents of the container in metered form, wherein the contents of the container comprise the ophthalmic formulation of claim 1.

32. A method for treating ocular hypertension comprising administering to a subject in need thereof a therapeutically effective amount of a formulation of claim 1.

33. A method for treating ocular hypertension comprising administering to a subject in need thereof a therapeutically effective amount of a formulation of claim 29.

34. A method for treating ocular hypertension comprising administering to a subject in need thereof a therapeutically effective amount of a formulation of claim 30.

* * * * *

UNITED STATES PATENT AND TRADEMARK OFFICE
CERTIFICATE OF CORRECTION

PATENT NO. : 8,952,051 B2
APPLICATION NO. : 12/939846
DATED : February 10, 2015
INVENTOR(S) : Anuradha V. Gore et al.

It is certified that error appears in the above-identified patent and that said Letters Patent is hereby corrected as shown below:

On the title page, item (56), in column 2, References Cited under "Other Publications", line 1, delete "non10n1c" and insert -- nonionic --, therefor.

On the title page, item (56), in column 2, References Cited under "Other Publications", line 2, delete "appl1cat10ns" and insert -- applications --, therefor.

On the title page, item (56), in column 2, References Cited under "Other Publications", line 2, delete "top1cal" and insert -- topical --, therefor.

On the title page, item (56), in column 2, References Cited under "Other Publications", line 2, delete "de11very"," and insert -- delivery", --, therefor.

In the Specification

In column 1, line 12, delete "2010," and insert -- 2009, --, therefor.

In column 1, line 46, delete "pupilary" and insert -- pupillary --, therefor.

In column 3, line 53, delete "cylcodextrin," and insert -- cyclodextrin, --, therefor.

In column 3, line 53, delete "polyoxythelene" and insert -- polyoxyethylene --, therefor.

In column 10, line 4, delete "bioerodable" and insert -- bioerodible --, therefor.

In column 10, line 5, delete "non-bioerodable" and insert -- non-bioerodible --, therefor.

In column 10, line 47, delete "phosphalipids," and insert -- phospholipids, --, therefor.

In column 10, line 47, delete "chloline," and insert -- choline, --, therefor.

In column 11, line 24, delete "cylcodextrin," and insert -- cyclodextrin, --, therefor.

In column 11, line 24, delete "polyoxythelene" and insert -- polyoxyethylene --, therefor.

In the Claims

In column 19, line 44, in claim 18, delete "cylcodextrin," and insert -- cyclodextrin, --, therefor.

Signed and Sealed this
Twenty-sixth Day of May, 2015

Michelle K. Lee
*Director of the United States Patent and Trademark Office*

CERTIFICATE OF CORRECTION (continued)
U.S. Pat. No. 8,952,051 B2

In column 19, lines 44-45, in claim 18, delete "polyoxythelene" and insert -- polyoxyethylene --, therefor.

In column 20, line 14, in claim 28, delete "is independently" and insert -- is --, therefor.

In column 20, line 15, in claim 29, delete "of comprising" and insert -- comprising --, therefor.

In column 20, line 50, in claim 30, delete "of comprising" and insert -- comprising --, therefor.